(12) United States Patent
Huang et al.

(10) Patent No.: US 11,266,464 B2
(45) Date of Patent: Mar. 8, 2022

(54) ANTENNA ASSEMBLY FOR MICROWAVE ABLATION AND MICROWAVE ABLATION NEEDLE USING THE SAME

(71) Applicant: Surgnova Healthcare Technologies (Zhejiang) Co., Ltd., Cixi (CN)

(72) Inventors: Wenxing Huang, Beijing (CN); Dezhi Zhan, Beijing (CN); Yong Yan, Beijing (CN); Hui Li, Beijing (CN)

(73) Assignee: Surgnova Healthcare Technologies (Zhejiang) Co., Ltd., Cixi (CN)

( * ) Notice: Subject to any disclaimer, the term of this patent is extended or adjusted under 35 U.S.C. 154(b) by 683 days.

(21) Appl. No.: 16/199,124

(22) Filed: Nov. 23, 2018

(65) Prior Publication Data
US 2019/0380777 A1    Dec. 19, 2019

Related U.S. Application Data

(63) Continuation of application No. PCT/CN2016/102870, filed on Oct. 21, 2016.

(30) Foreign Application Priority Data

May 24, 2016    (CN) .......................... 201610348040.4

(51) Int. Cl.
  *A61B 18/18*    (2006.01)
  *A61L 31/02*    (2006.01)
  *A61B 18/00*    (2006.01)

(52) U.S. Cl.
  CPC ........ *A61B 18/1815* (2013.01); *A61L 31/022* (2013.01); *A61B 2018/00023* (2013.01);
  (Continued)

(58) Field of Classification Search
  CPC ................ A61B 18/18; A61B 18/1815; A61B 2018/183; A61B 2018/1838;
  (Continued)

(56) References Cited

U.S. PATENT DOCUMENTS

| 4,700,716 A | 10/1987 | Kasevich et al. |
| 5,026,959 A | 6/1991 | Ito et al. |

(Continued)

FOREIGN PATENT DOCUMENTS

| CN | 1489807 A | 4/2004 |
| CN | 101926046 A | 12/2010 |

(Continued)

OTHER PUBLICATIONS

International Search Report dated Jan. 25, 2017 in connection with International application No. PCT/CN2016/102870.
(Continued)

*Primary Examiner* — Thomas A Giuliani
(74) *Attorney, Agent, or Firm* — Hamre, Schumann, Mueller & Larson, P.C.

(57) ABSTRACT

An antenna assembly for microwave ablation can include a radiator for emitting a microwave for ablation; a coaxial cable for transmitting the microwave for ablation generated by a microwave generator to the radiator; an annular composite structure is provided around the coaxial cable for inhibiting an electromagnetic wave from propagating backwards along the coaxial cable. In some embodiment, the annular composite structure comprises an annular nonmetallic layer and an annular metallic layer located outside the annular nonmetallic layer. In some embodiments, the annular metallic layer is electrically insulated from the coaxial cable. In some embodiments, the antenna assembly can be used with a microwave ablation needle. The annular composite structure can inhibit the backward propagation of the microwave along the coaxial cable exterior wall. In some embodiments, circulation water enters the radiation zone, to avoid high temperatures of the head the ablation needle.

18 Claims, 3 Drawing Sheets

(52) U.S. Cl.
CPC ............. *A61B 2018/00577* (2013.01); *A61B 2018/00791* (2013.01); *A61B 2018/1838* (2013.01); *A61B 2018/1869* (2013.01)

(58) Field of Classification Search
CPC .... A61B 2018/1861; A61B 2018/1869; A61B 2018/1876; A61B 2018/1884; A61B 2018/1892; A61B 2018/00023; A61N 5/02
USPC ........................... 606/33; 607/101, 154, 156
See application file for complete search history.

(56) References Cited

U.S. PATENT DOCUMENTS

| | | | |
|---|---|---|---|
| 2007/0049917 A1 | 3/2007 | Yang et al. | |
| 2010/0097284 A1 | 4/2010 | Brannan et al. | |
| 2011/0066144 A1* | 3/2011 | Bonn | A61B 18/18 606/33 |
| 2011/0077635 A1 | 3/2011 | Bonn | |
| 2011/0077639 A1* | 3/2011 | Brannan | A61B 18/1815 606/33 |
| 2012/0172863 A1 | 7/2012 | Brannan | |
| 2014/0155881 A1 | 6/2014 | Prakash et al. | |
| 2015/0057651 A1 | 2/2015 | Bonn | |
| 2020/0069368 A1* | 3/2020 | Huang | A61B 18/1815 |

FOREIGN PATENT DOCUMENTS

| | | | |
|---|---|---|---|
| CN | 202386782 U | * | 8/2012 |
| CN | 102727306 A | | 10/2012 |
| CN | 103142307 A | | 6/2013 |
| CN | 103717166 A | | 4/2014 |
| CN | 104688335 A | | 6/2015 |
| CN | 204581504 U | | 8/2015 |
| CN | 105361949 A | | 3/2016 |
| CN | 105816240 A | | 8/2016 |
| CN | 205885525 U | | 1/2017 |
| WO | 2013121403 A1 | | 8/2013 |
| WO | 2016029022 A1 | | 2/2016 |

OTHER PUBLICATIONS

Office Action dated Oct. 27, 2017 in connection with Chinese application No. 201610348040.4.
Extended European Search Report dated Jan. 17, 2020 in connection with European App. No. 16902938.6.

* cited by examiner

ANTENNA ASSEMBLY FOR MICROWAVE ABLATION AND MICROWAVE ABLATION NEEDLE USING THE SAME

CROSS-REFERENCE TO RELATED APPLICATIONS

This application is a continuation of International Application No. PCT/CN2016/102870 having an international filing date of Oct. 21, 2016 entitled "ANTENNA ASSEMBLY FOR MICROWAVE ABLATION AND MICROWAVE ABLATION NEEDLE USING THE SAME". The '870 international application claimed priority benefits, in turn, from Chinese Patent Application No. 201610348040.4 filed on May 24, 2016. The '870 international application is hereby incorporated by reference herein in its entirety.

FIELD OF THE INVENTION

This disclosure relates to the technical field of microwave treatment devices, in particular, to an antenna assembly for microwave ablation and a microwave ablation needle using the same.

In recent years, microwave ablation has become an important treatment means for treating liver cancer. Microwave ablation uses the heat effect of microwaves in polar molecules, such as water, to heat the pathology area to a high temperature instantaneously, so that the issue is solidified and necrosed by dewatering, thereby achieving a treatment purpose.

Concerning the design of microwave antenna, there are currently two types of ablation needles that are popular in the market. One type is ablation antennas that do not use choke technology, such as disclosed in Chinese Patent Application Publication No. CN103142307A. The other type are ablation antennas using a choke ring (groove), such as those disclosed in Chinese Patent Application Publication No. CN104688335A, of which the main structure is shown in FIG. 1.

When choke technology is not used, some microwaves will escape backwards along the outside surface of the exterior conductor of the coaxial cable, thereby resulting in that ablation zone becoming an ellipsoidal shape. The ablation antenna using a choke ring (groove) can inhibit the backward escaping of the microwave and obtain a rounder ablation zone. However, in order to stabilize the performance of the choke ring (groove), it is required to fill a high dielectric constant medium stable with respect to temperature. This results in the circulation water not arriving at the head of the ablation needle. Excessively high temperatures of the head of the needle tend to burn the ablation needle out and/or crack the ablation needle possibly causing a medical accident.

SUMMARY OF INVENTION

In view of above issues with the current technology, an antenna assembly for microwave ablation and a microwave ablation needle using the same is disclosed below.

In order to achieve the above-mentioned object, in some embodiments an antenna assembly for microwave ablation can comprise:

a radiator for emitting a microwave for ablation;

a coaxial cable for transmitting the microwave for ablation generated by a microwave generator to the radiator;

wherein an annular composite structure for inhibiting an electromagnetic wave propagated backwards along the coaxial cable is provided around the coaxial cable, wherein the annular composite structure comprises an annular nonmetallic layer and an annular metallic layer located outside the annular nonmetallic layer, wherein the annular metallic layer is electrically insulated from the coaxial cable.

As some preferred embodiments, where a direction where the radiator lies is a front end of the metallic layer and an opposite direction thereof is a back end of the metallic layer, a length $L_1$ of the metallic layer in the annular composite structure and a distance $L_2$ between a feeding point and the back end of the metallic layer satisfy the following relationship:

$$\sqrt{\epsilon_1}L_1 - \sqrt{\epsilon_2}[L_2-(L_1-L_2)] \approx C/2f$$

wherein $\epsilon_1$ is a relative permittivity of a human tissue, $\epsilon_2$ is a relative permittivity of a material of the annular nonmetallic layer, C is the light velocity in vacuum, and f is a frequency of the microwave; wherein the difference between the both sides of the formula is within ±20%.

In some preferred embodiments, a distance $L_3$ from the front end of the metallic layer to the most front end of the radiator and the $L_1$ further satisfy the following relationship:

$$L_1 \approx L_3$$

wherein the difference between the both sides of the formula mentioned above is within ±20%.

In some preferred embodiments, material of the annular metallic layer is copper, iron, aluminum, gold, silver, palladium, platinum, tin, nickel, zinc, or an alloy thereof.

In some preferred embodiments, the annular composite structure has a total thickness between and inclusive of 0.001 to 2 mm.

In some preferred embodiments, for an antenna assembly having a frequency of 2.45 GHz, the length L1 of the annular metallic layer is between and inclusive of 5 mm and 25 mm.

In some preferred embodiments, the antenna assembly further comprises a cooling channel for cooling the radiator. In some preferred embodiments, the cooling channel is preferably able to transport a cooling medium to the most front end of the radiator so as to cool the whole radiator.

In some preferred embodiments, the cooling channel is of nonmetallic material. In some preferred embodiments, the cooling channel is made of polytetrafluoroethylene (PTFE) material.

In some preferred embodiments, the annular metallic layer is formed on an exterior wall of the cooling channel provided around the coaxial cable by wrapping and/or adhering a metallic foil processed as a thin layer around the exterior wall of the cooling channel provided around the coaxial cable and/or by a sputtering process, an electroplating process and/or an electroless plating process, so that the annular metallic layer and the cooling channel of nonmetallic material together build at least part, if not all, of the annular composite structure.

In some preferred embodiments, a radiation zone of the antenna assembly is not filled by any high dielectric constant solid medium having a relative permittivity of 25 or more.

In some preferred embodiments, the radiator is a metallic cap or an extended section of an inner core of the coaxial cable.

In some preferred embodiments, the antenna assembly further comprises a temperature detector for detecting a temperature of the radiator.

In some embodiments, a microwave ablation needle, can comprise the antenna assembly as mentioned above.

As can be seen from the above-, the disclosed antenna assembly and microwave ablation needle can have the following advantageous effects: (1) the annular composite structure can inhibit microwaves from being propagated backwards along the coaxial cable and an exterior wall of a water inlet pipe effectively; and (2) the disclosed antenna assembly and microwave ablation needle can make it unnecessary to fill a stabilizing medium in a radiation zone by a choke technology using the annular composite structure, so that the circulation water enters the radiation zone through the annular composite structure (choke structure), and the temperatures of the head of the ablation needle and the needle stem can be controlled effectively, so as to avoid burnout of the ablation needle and medical accidents due to excessively high temperatures.

DETAILED DESCRIPTION OF PREFERRED EMBODIMENT(S)

Figure 1:
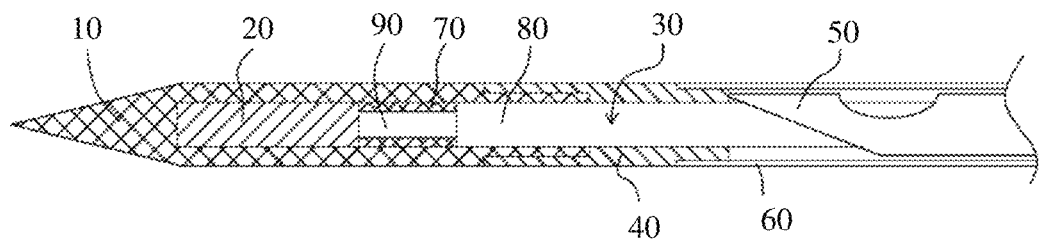
FIG. 1 is a schematic drawing of a main structure of a prior art antenna assembly for microwave ablation.

An antenna assembly for microwave ablation can comprise: a radiator and a coaxial cable, wherein the radiator is for emitting a microwave for ablation and the coaxial cable is for transmitting the microwave for ablation generated by a microwave generator to the radiator; wherein an annular composite structure for inhibiting an electromagnetic wave propagated backwards along the coaxial cable is provided around the coaxial cable, wherein the annular composite structure comprises an annular nonmetallic layer and an annular metallic layer located outside the annular nonmetallic layer, wherein the annular metallic layer is electrically insulated from the coaxial cable. In some preferred embodiments, the annular composite structure can comprise the two layers mentioned above only, or can further comprise more layers, such as a further nonmetallic layer outside the annular metallic layer.

The annular metallic layer can be made by using various conductive metals, for example, copper, iron, aluminum, gold, silver, palladium, platinum, tin, nickel, zinc, or an alloy thereof. For example, in embodiments, using copper, a copper foil, a material plated by copper by sputtering, a copper-plated material, is used preferably, for example, by wrapping or adhering a metallic foil processed as a thin layer around the exterior wall of the nonmetallic layer, by forming a thin metallic layer on the outside surface of the nonmetallic layer by a process, such as sputtering, and/or by forming a thin metallic layer on the outside surface of the nonmetallic layer by a process, such as electroplating or electroless plating.

In at least some embodiments, the shape of the annular metallic layer changes with the outline of the water inlet pipe. Generally, it has an annular shape, with a thickness between and inclusive of 0.001 mm to 2 mm. In some preferred embodiments, the thickness is 0.05 mm. In at least some embodiments the length which is not limited to but is preferably about half (in human tissue) of the wavelength of the electromagnetic wave propagated backwards along the coaxial cable. For a frequency of 2.45 GHz, the length is between and inclusive of 5 mm to 25 mm, preferably 11 mm.

In some embodiments, the annular composite structure can be provided as a ring around the coaxial cable, which can be provided against the coaxial cable closely, or can be provided to keep a distance to the coaxial cable, for example, a distance being twice of the diameter of the coaxial cable. In most, if not all embodiments, the annular metallic layer in the annular composite structure is electrically insulated from the coaxial cable. In at least some embodiments, the total thickness of the annular composite structure is between and inclusive of 0.001 mm to 2 mm. In some preferred embodiments, a cooling channel can be formed outside the coaxial cable by using a form of an encircled nonmetallic flexible tube. In at least some embodiments, the cooling channel is used to pass the cooling medium flowing in through the interior wall gap and pass the cooling medium flowing out through the exterior wall gap. In at least some embodiments, the cooling medium is used to cool a part or all of the radiation zone including the radiator. In some embodiment, it is possible to use the cooling channel as the nonmetallic layer of the annular composite structure, and to form the annular composite structure together by a metallic layer provided on the outside surface thereof. In some preferred embodiments, the cooling channel is of PTFE (polytetrafluoroethylene) material. In some embodiments, in order to enhance the strength of the cooling channel, a stainless-steel pipe can be used in a connection section thereof. In most, if not all embodiments, the annular metallic layer should be formed on the outside surface of the cooling channel of the PTFE material.

In some embodiments, the radiation zone of the antenna assembly may not be filled by a high dielectric constant medium, such as, high permittivity ceramic materials having a relative permittivity of 25 or more, such as zirconium oxide, or the like.

In the above-mentioned antenna assembly, the radiator can be a metallic cap, for example, a copper cap, or can be an extended section of an inner core of the coaxial cable. In some, if not all embodiments, the lengths of both are designed to be the same.

In at least some embodiments, when a direction where the radiator lies, i.e. the direction of the head of the antenna assembly, is a front end of the metallic layer and an opposite direction thereof is a back end of the metallic layer, a length $L_1$ of the annular metallic layer and a distance $L_2$ between a feeding point and the back end of the annular metallic layer substantially satisfy the following relationship:

$$\sqrt{\epsilon_1}L_1 - \sqrt{\epsilon_2}[L_2 - (L_1 - L_2)] \approx C/2f$$

wherein $\epsilon_1$ is a relative permittivity of a human tissue, $\epsilon_2$ is a relative permittivity of a material of the annular nonmetallic layer, C is the light velocity in vacuum, and f is a frequency of the microwave. The difference between both sides of the formula mentioned above is within ±40%, preferably within ±20%.

Further, the length $L_1$ of the annular metallic layer and a distance $L_3$ from the front end of the annular metallic layer to the front end of the radiator substantially satisfy the following relationship:

$$L_1 \approx L_3 \quad (2)$$

wherein the difference between the both sides of the formula mentioned above is within ±40%, preferably within ±20%.

The design of the above-mentioned antenna allows for the cooling medium, for example, the circulation water arriving at the head of the antenna (copper cap). Therefore, after the ablation has been carried out for a period of time, the human tissue around the antenna is carbonized, and the relative permittivity thereof decreases. Then, instead of the human tissue, the circulation water keeps $\epsilon_1$ at a relatively high value, thereby maintaining the relationship described above, $\sqrt{\epsilon_1}L_1 - \sqrt{\epsilon_2}[L_2 - (L_1 - L_2)] \approx C/2f$, while still establishing, and maintaining the choke property of the antenna. By using the annular composite structure for choking, the antenna assembly corresponds to a symmetrical full-wave dipole antenna, which has a more uniform near field distribution than a half-wave dipole antenna.

In some preferred embodiment, the antenna assembly further comprises a temperature detector for detecting a temperature of the radiator. In some embodiments, the temperature detector is preferably connected to a control circuit. When a temperature exceeding a certain threshold is detected, means, such as increasing the flow rate of the cooling medium in the cooling channel and/or decreasing the emission power of the radiator, can be used to prevent excessive rise of the radiator temperature. This can prevent, or at least reduce both burnout of the radiator and/or damage to the human body.

In some embodiments, a microwave ablation needle can include the antenna assembly as mentioned above.

FIG. 1 is example of a prior art ablation antenna disclosed in Chinese Patent Application Publication No. CN104688335A. Prior art ablation antenna consists of zirconia thorn 10, pole core 20, coaxial cable 30, choke ring 40, water pipe 50, needle bar 60, epoxy glue 70, outer conductor 80, and dielectric layer 90.

Figure 2:
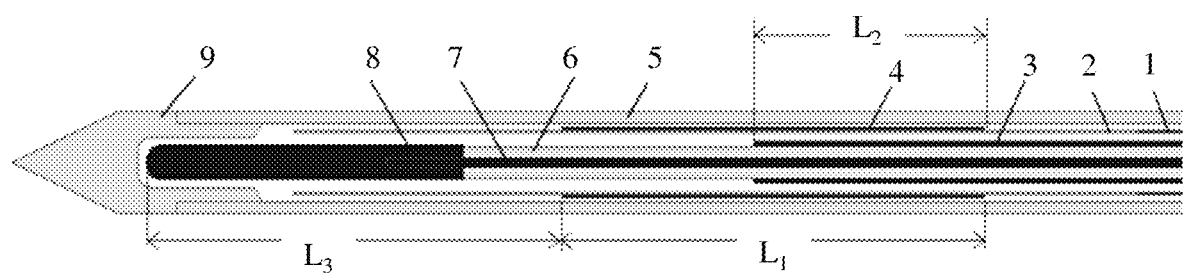
FIG. 2 is a schematic drawing of a main structure of an antenna assembly for microwave ablation.

FIG. 2 is a schematic drawing of a structure of a preferred embodiment of an antenna assembly. The antenna assembly can include stainless-steel water inlet pipe section 1, PTFE water inlet pipe section 2, coaxial cable exterior conductor 3, copper foil 4, glass fiber outside pipe 5, coaxial cable medium layer 6, coaxial cable inner core 7, copper cap 8 and ceramic prick head 9. Among these, the water inlet pipe comprises stainless-steel water inlet pipe section 1 and PTFE water inlet pipe section 2, wherein stainless-steel water inlet pipe section 1 is connected to PTFE water inlet pipe section 2 in a radiation zone of the antenna. The circulation water flows to the antenna head through the gap between the water inlet pipe and the coaxial cable and flows out from the gap between glass fiber outside pipe 5 and water inlet pipe. In at least some embodiments, copper foil 4 is against the exterior wall of the PTFE water inlet pipe section 2, and copper cap 8 is welded to coaxial cable inner core 7.

If there is no copper foil 4 in the water inlet pipe in the antenna structure, after the microwave arrives at the feeding point (the end of the coaxial cable exterior conductor), a part of the microwave is transmitted forwards along coaxial cable inner core 7 and radiates into the ambient tissue or another medium by copper cap 8, while other parts is transmitted backwards along the outside surface of coaxial cable exterior conductor 3 in the outside tissue, circulation water, PTFE of the inner pipe and glass fiber of the outside pipe and radiates into the ambient tissue at the same time. This can result in that the microwave ablation zone becoming an ellipsoidal shape. In the current antenna assembly, since a length of copper foil covers the water inlet pipe, the microwave propagated backwards are divided into two components. One microwave component is transmitted in the tissue along the outside wall of copper foil 4, while the other microwave component is propagated along the inner wall of copper foil 4 and coaxial cable exterior conductor 3 in PTFE water inlet pipe section 2. The energy of the microwave propagated in the circulation water is negligible.

Since the relative dielectric constant of the human tissue (about 40) is many times higher than that of the PTFE medium (about 2.5), the phase difference between the two microwave components is larger when the propagation distance along copper foil 4 is larger. When copper foil 4 with an appropriate length (slightly larger than a half of the wave length of the microwave in the human tissue) is used, it is possible to allow the two microwave components to have a half-cycle difference and to be opposite with each other. At the same time, the position of the copper foil with respect to the feeding point can be adjusted, so that the amplitudes of the two microwave components are the same. Thus, when the two microwave components meet at the end of the copper foil, they cancel each other out due to their same amplitudes and opposite phases. In these embodiments, the microwave is cut off at the end of copper foil 4 and does not continue to be propagated backwards along the coaxial cable.

Thus, the microwave can be concentrated in the zone around the copper foil and the copper cap to perform ablation. Therefore, a rounder ablation zone can be obtained by this kind of ablation antenna.

Modifications to the embodiments described above are possible. For example:

(1) A main function of the copper cap is to extend and reinforce the coaxial cable inner core. It is possible to just use a coaxial cable inner core.

(2) Another nonmetallic material having a low dielectric constant (less than 3) can be used for PTEF water inlet pipe section 2, while the length and position of the copper foil might need to be adjusted.

(3) The materials and thicknesses of the outside pipe and the prick head can be selected according to practical conditions. In most, if not all embodiments, the materials of the water inlet pipe and the outside pipe are of nonmetallic material in the radiation zone of the antenna.

(4) Another process can be used to cover the water inlet pipe with the copper foil, for example, by plating a film of metal on the water inlet pipe.

Figure 3:
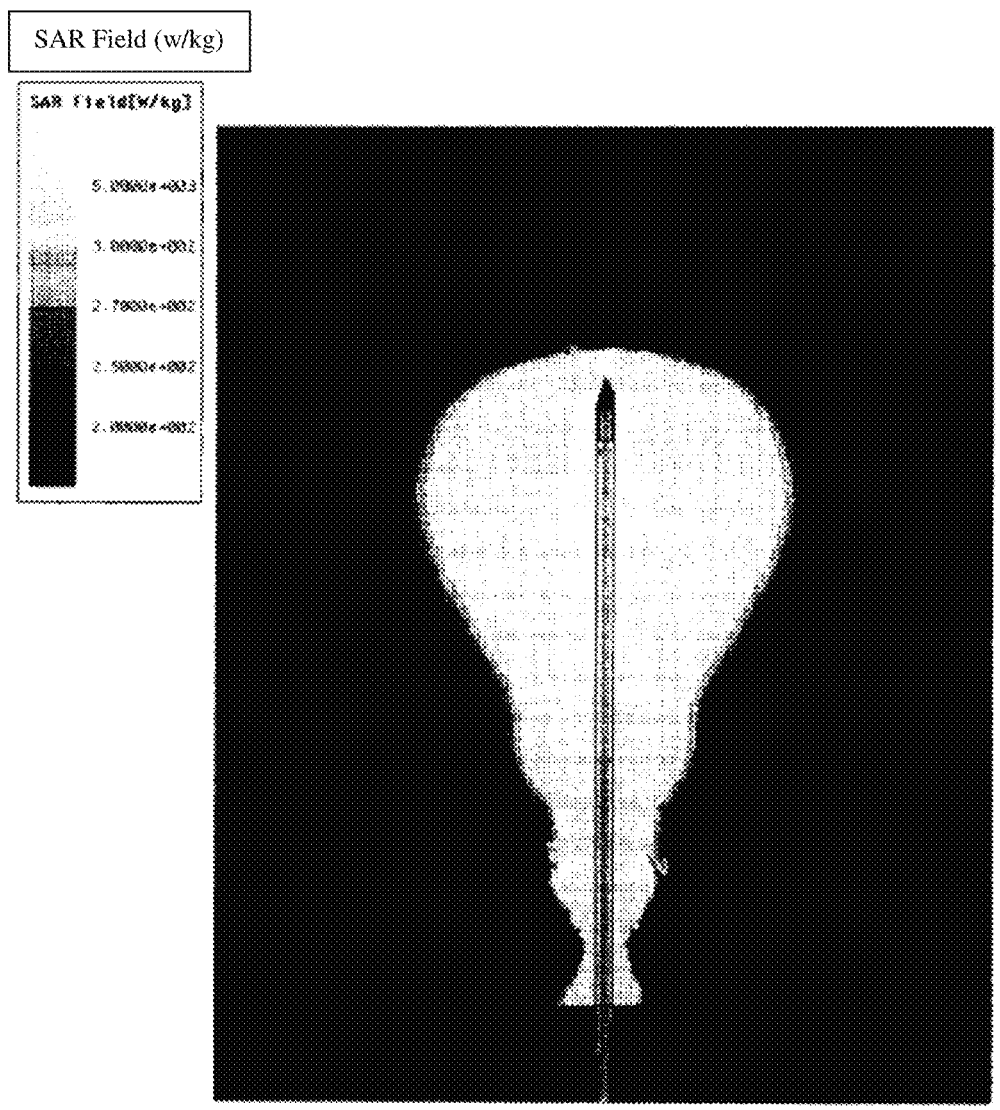
FIG. 3 is a distribution diagrams of the absorption field of the ablation antenna in the case where there is no annular composite structure and FIG. 4 is a distribution diagrams of the absorption field of the ablation antenna in the case where there is an annular composite structure.
Figure 4:
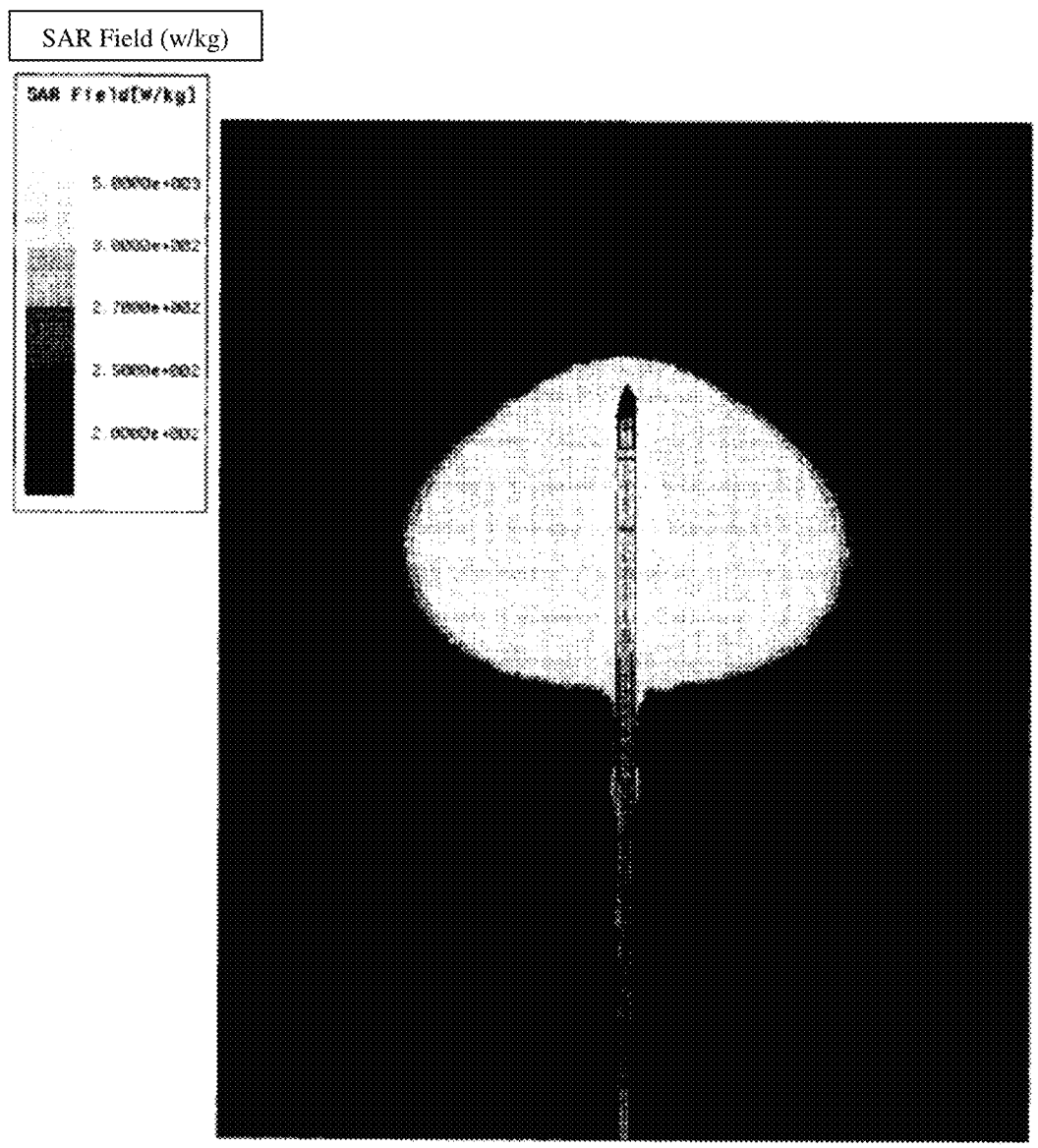

By experimental validation, the distributions of the absorption fields in both cased where there is no annular composite structure and cased where there is the annular composite structure are shown in FIG. 3 and FIG. 4. As can be seen therefrom, the antenna design can effectively inhibit the backward propagation of the microwave along the coaxial cable exterior wall and obtain a relatively spherical ablation zone. Meanwhile, in the ablation antenna, it is not required to fill any stabilizing medium in the radiation zone. The circulation water is allowed to enter the radiation zone, so that the temperature of the head the ablation needle can be controlled effectively, so as to avoid burnout of the ablation needle and medical accident due to excessively high temperatures.

The purposes, technical solutions and advantageous effects of this disclosure are described in details by the above-mentioned specific examples. It should be understood that the contents above are merely specific examples of this disclosure and should not be used to limit this disclosure. Any modification, equivalent replacement, improvement, and the like in the spirit and principle of this disclosure should be included in the protection scope of this disclosure.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. An antenna assembly for microwave ablation, comprising:
   (a) a radiator for emitting a microwave;
   (b) a coaxial cable for transmitting said microwave generated by a microwave generator to said radiator;
   wherein an annular composite structure for inhibiting an electromagnetic wave propagated backwards along the coaxial cable is provided around said coaxial cable, wherein said annular composite structure comprises an annular nonmetallic layer and an annular metallic layer located outside said annular nonmetallic layer, wherein said annular metallic layer is electrically insulated from said coaxial cable, and
   wherein where a direction where the radiator lies is a front end of said metallic layer and an opposite direction thereof is a back end of said metallic layer, a length $L_1$ of said metallic layer in said annular composite structure and a distance $L_2$ between a feeding point and said back end of the metallic layer satisfy a first formula, wherein said first formula is $$\sqrt{\epsilon_1}L_1 - \sqrt{\epsilon_2}[L_2-(L_1-L_2)] \approx C/2f$$

wherein $\epsilon_1$ is a relative permittivity of a human tissue, $\epsilon_2$ is a relative permittivity of a material of said annular nonmetallic layer, C is the light velocity in vacuum, and f is a frequency of said microwave.

2. The antenna assembly according to claim 1, wherein a difference between both sides of said first formula mentioned is within ±20%.

3. The antenna assembly according to claim 1, wherein a distance L3 from the front end of the metallic layer to a most front end of the radiator and the L1 further satisfy a second formula, wherein said second formula is $$L_1 \approx L_3$$

4. The antenna assembly according to claim 3, wherein a difference between both sides of said second formula is within ±20%.

5. The antenna assembly according to claim 3, wherein a difference between both sides of said second formula is within ±40%.

6. The antenna assembly according to claim 1, wherein said antenna assembly has a frequency of 2.45 GHz and said length L1 of said annular metallic layer is between and inclusive of 5 mm and 25 mm.

7. The antenna assembly according to claim 1, wherein a material of the annular metallic layer is copper, iron, aluminum, gold, silver, palladium, platinum, tin, nickel, zinc, or an alloy thereof.

8. The antenna assembly according to claim 1, wherein said annular composite structure has a total thickness between and inclusive of 0.001 mm to 2 mm.

9. The antenna assembly according to claim 1, further comprising a cooling channel for cooling said radiator.

10. The antenna assembly according to claim 9, wherein said cooling channel is able to transport a cooling medium to a most front end of said radiator so as to cool the whole radiator.

11. The antenna assembly according to claim 9, wherein said cooling channel is made of a nonmetallic material.

12. The antenna assembly according to claim 11, wherein said cooling channel is made of PTFE.

13. The antenna assembly according to claim 9, wherein said annular metallic layer is formed on an exterior wall of said cooling channel provided around the coaxial cable by wrapping or adhering a metallic foil processed as a thin layer around the exterior wall of the cooling channel provided around the coaxial cable or by a sputtering process, an electroplating process or an electroless plating process, so that said annular metallic layer and said cooling channel together build at least a part of said annular composite structure.

14. The antenna assembly according to claim 1, wherein any solid medium filling a radiation zone of said antenna assembly has a relative permittivity of under 25.

15. The antenna assembly according to claim 1, wherein said radiator is a metallic cap or an extended section of an inner core of the coaxial cable.

16. The antenna assembly according to claim 1, further comprising:
   (c) a temperature detector for detecting a temperature of the radiator.

17. The antenna assembly according to claim 1, wherein a difference between both sides of said first formula mentioned is within ±40%.

18. A microwave ablation needle, comprising:
   (a) an antenna assembly comprising:
      (i) a radiator for emitting a microwave;
      (ii) a coaxial cable for transmitting said microwave generated by a microwave generator to said radiator;
   wherein an annular composite structure for inhibiting an electromagnetic wave propagated backwards along the coaxial cable is provided around said coaxial cable, wherein said annular composite structure comprises an annular nonmetallic layer and an annular metallic layer located outside said annular nonmetallic layer, wherein said annular metallic layer is electrically insulated from said coaxial cable, and
   wherein where a direction where the radiator lies is a front end of said metallic layer and an opposite direction thereof is a back end of said metallic layer, a length $L_1$ of said metallic layer in said annular composite structure and a distance $L_2$ between a feeding point and said back end of the metallic layer satisfy a first formula, wherein said first formula is $$\sqrt{\epsilon_1}L_1 - \sqrt{\epsilon_2}[L_2-(L_1-L_2)] \approx C/2f$$

wherein $\epsilon_1$ is a relative permittivity of a human tissue, $\epsilon_2$ is a relative permittivity of a material of said annular nonmetallic layer, C is the light velocity in vacuum, and f is a frequency of said microwave.

* * * * *